United States Patent [19]

Hayashi

[11] Patent Number: 5,145,680
[45] Date of Patent: Sep. 8, 1992

[54] EYE DROP FORMULATION USEFUL FOR TREATING LESIONS OF CORNEAL EPITHELIUM

[75] Inventor: Masao Hayashi, 3-23-7-202, Otsuka, Bunkyo-ku, Tokyo 112, Japan

[73] Assignees: Masao Hayashi; Nisshin Flour Milling Co., Ltd., both of Tokyo, Japan; a part interest

[21] Appl. No.: 594,094

[22] Filed: Oct. 9, 1990

[30] Foreign Application Priority Data

Feb. 13, 1989 [JP] Japan ................................. 1-31098
Feb. 13, 1990 [WO] PCT Int'l Appl. .....PCT/JP90/00173

[51] Int. Cl.$^5$ .......................... C07K 1/02; C07K 15/06
[52] U.S. Cl. ................................. 424/427; 424/422; 514/8; 514/912; 514/914; 514/915; 530/395; 530/830
[58] Field of Search ..................... 424/422, 427, 428; 514/8, 912, 914, 915; 530/395, 830

[56] References Cited

FOREIGN PATENT DOCUMENTS 0179477 4/1986 European Pat. Off. .
240031 10/1987 European Pat. Off. .
292663 11/1988 European Pat. Off. .

OTHER PUBLICATIONS

"Effect of vitronectin on the healing of rabbit corneal epithelial damage", Kabata et al., Nippon Ganka Gakkai Zasshi (Japan), May 1990, 94(5) pp. 457–461 (Abstract) Abstract only.

Primary Examiner—Thurman K. Page
Assistant Examiner—Carlos Azpuru
Attorney, Agent, or Firm—Abelman Frayne & Schwab

[57] ABSTRACT

Vitronectin produces very high therapeutic effects upon injuries of the corneal epithelium. When applied to lesions of the corneal epithelium in the form of eye drops, Vitronectin induces rapid cure of the lesions with regeneration of normal cells. Moreover Vitronectin can be sterilized by autoclaving.

2 Claims, 1 Drawing Sheet

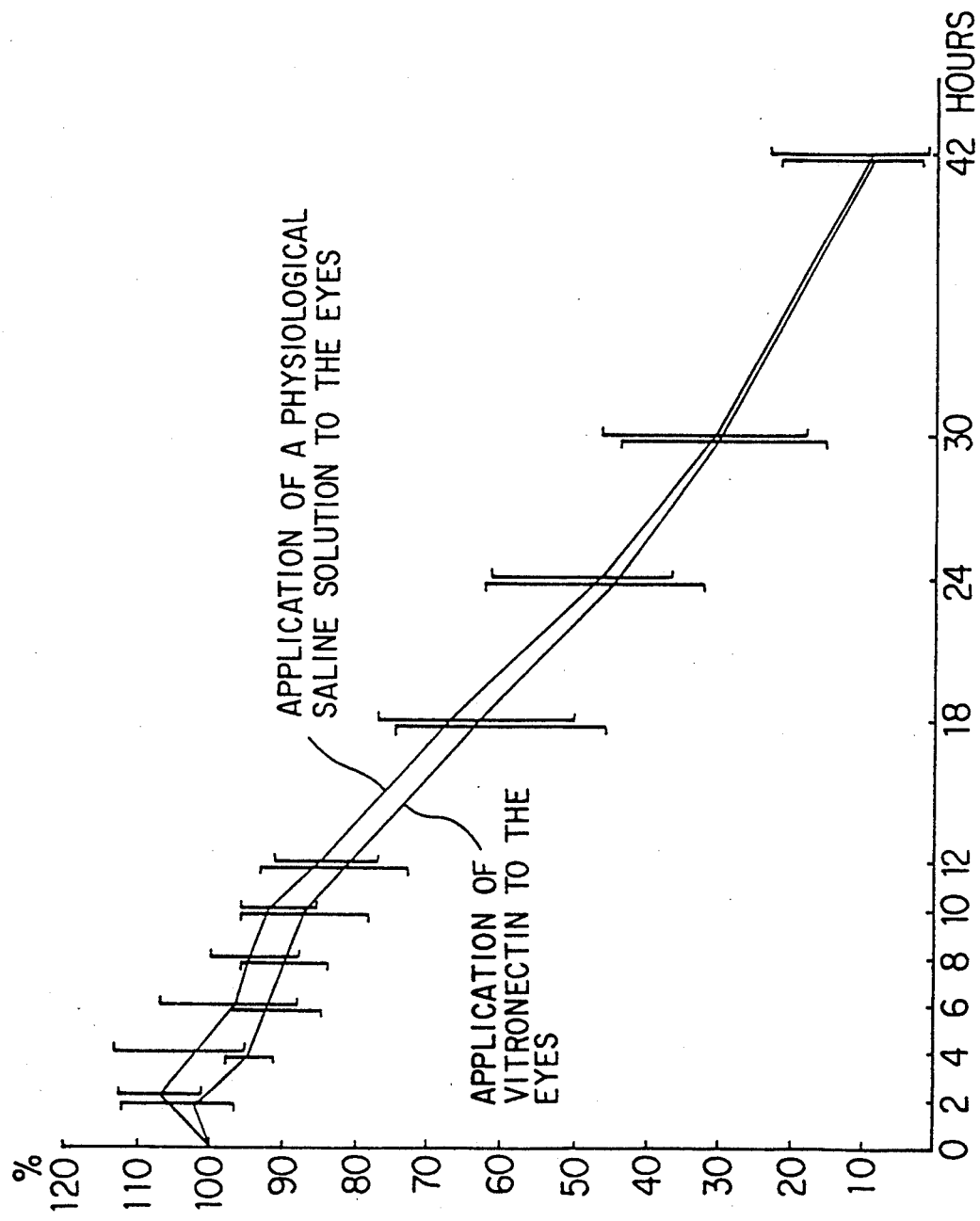

EYE DROP FORMULATION USEFUL FOR TREATING LESIONS OF CORNEAL EPITHELIUM

CROSS-REFERENCE TO RELATED APPLICATIONS

This application is related to PCT/JP90/00173 filed Feb. 13, 1990, which is based on Japanese Patent Application No. 31098/89, filed Feb. 13, 1989.

FIELD OF INDUSTRIAL APPLICATION

This invention relates to an eye drop formulation which may effectively be used for curing injuries of corneal epithelium and particularly is concerned with an eye drop formulation useful for treating lesions of corneal epithelium without causing adverse reactions in the course of healing said lesions.

PRIOR ART AND PROBLEM TO BE SOLVED

In recent years new eye drops such as one containing a steroid or an antibiotic have successively been developed. These eye drops, however, are often applied to a patient's eyes at a high concentration in order to penetrate into eye tissues. Consequently, application of some of the eye drops to a patient's eyes produce adverse reactions such as delay in healing or regeneration of abnormal epithelia cells in the defective region.

On the other hand, fibronectin which is a glycoprotein present in plasma and cell surface not only promote growth of the corneal epithelium cells but also enhance adhesion of the same and are considered to be curative for lesions of the corneal epithelium. Some cases reported where fibronectin was applied in the treatment for intractable lesions of the corneal epithelium.

Fibronectin is, however, unstable to heat, and are difficult to be sterilized by autoclaving. It is also reported that the efficacy of fibronectin is questionable.

As a result of extensive studies to develop eye drop formulations for the effective use in treating lesions of the corneal epithelium without the above-mentioned adverse reactions, the present inventor has found that Vitronectin which is glycoprotein having cell adhesion-enhancing activities similar to those of fibronectin can exhibit very high curativeness for injuries of the corneal epithelium with no adverse reaction. This invention has been completed on the basis of the above finding. An object of the invention is to provide an eye drop formulation suitably used for the cure of lesions of the coroneal epithelium without adverse reaction.

MEANS FOR SOLVING THE PROBLEM

This invention is directed to an eye drop formulation containing Vitronectin for the treatment of injuries of the corneal epithelium.

Lesions of the corneal epithelium to which the eye drop formulation of the invention is applicable mean wound and erosion formed on coroneal epithelium which include, for example, wound and erosion caused by misuse of contact lens or wound and erosion occurring in so-called dry eye patients who suffer from difficulty in moisting eyes.

Vitronectin is a glycoprotein present in blood of animals and play an important role in cell adhesion, blood coagulation, immunological complement, cancer metastasis, and etc. Effectiveness of Vitronectin as a medicament has heretofore been not known at all.

Vitronectin used in the invention is collected from human blood and purified. A preferred method of collecting and purifying vitronectin from human blood has already been proposed by the present inventor wherein Vitronectin present in organisms, for example, in plasma is purified by specifically binding it to a glycosaminoglycan-fixed carrier in the presence of urea (see Japanese Patent Application No. 125990/1988). Unlike the fibronectin, the glycoprotein, as described above, the collected and purified Vitronectin is heat resistant and may be sterilized by autoclaving to kill possibly coexisting hepatitis viruses and others. It is therefore preferable to use the Vitronectin sterilized by autoclaving. The sterilization is carried out preferably under conditions as specified in Japanese Pharmacopeia, for example, at 115° C. for 30 min., at 121° C. for 20 min. or at 126° C. for 15 min.

In preparing an eye drop formulation, the Vitronectin thus obtained is duluted by addition of a physiological saline solution or a buffer solution to a concentration of 0.1 µg/ml–500 µg/ml, preferably 10 µg/ml –200 µg/ml. At concentrations below 0.1 µg/ml the efficacy will not sufficiently be high, and at concentrations higher than 500 µg/ml it will not significantly be superior. The eye drop dosage is satisfactorily one drop (about 50 µl) per dose, several times a day.

An experimental example of the curative effect of Vitronectin on lesions of the coroneal epithelium in 12 white rabbits will be shown below.

Experimental method: A circular epithalaxic lesion 6.5 mm in diameter was formed at the center of the coronea in each of 24 eyes of 12 white rabbits. Immediately after formation of the epithalaxia, Vitronectin was applied to one eye and a physiological saline solution to the other eye. The Vitronectin was prepared in the form of an eye drop formulation by sterilizing Vitronectin purified from rabbit plasma by autoclaving at 121° C. for 20 min. and diluting the sterilized Vitronectin with a sterilized physiological saline solution to a Vitronectin concentration of 200 µg/ml. The eye drops were applied to the eye every hour for 12 hours and subsequently every six hours for a total of 48 hours. On applying the eye drops photographs were taken to measure remaining area of the epithalaxic lesion.

The results are shown in FIG. 1 in which the horizontal axis represents hours from the initiation of the eye drop application, and the vertical axis percent change of the lesional area.

It was indicated by the above results that 4–6 hours after formation of the epithalaxic lesion defective area of the epithelium was significantly smaller in the Vitronectin-treated eye than in the physiological saline solution-treated eyes, or that eye drop application of Vitronectin is effective in the epithelial defect model of the rabbit normal cornea at the early curative stage of the lesion.

Examples of clinical use of the Vitronectin eye drop formulation of the invention will be given below to describe the invention in more detail.

Examples of the clinical use

1. H. K., 35-year-old female

Disease: Recurrent erosion of the corneal epithelium

The patient was scratched at her left eye by her child on Jun. 9, 1988. She visited a nearby physician by whom erosion of the corneal epithelium was pointed out. The epithelium was detached once a week after temporary releaf. Said physician prescribed vitamin and chondroitin eye drops. An eye ointment was also used at night. However, she suffered from repeated recurrence and on September 5 she made her first visit to the hospital attached to Tsukuba University.

Visual acuity, right 1.0 (n.c.), left 0.6 (n.c.)

Spotted inflammation on the superficial membrane localized at the lower right portion of the left eye was observed.

Progress: On September 12, pathological epithelium was curetted due to recurrence of the detachment.

Subsequently the patient was examined with conservative treatment applied. Regenerated epithelium was pathological. On September 14, the pathological epithelium was again curetted followed by application of Vitronectin eye drops (200 µg/ml). After the curettement, the patient was instructed to apply the Vitronectin eye drops every one hour and eye ointment when she went to bed. Normal epithelium was regenerated on September 19, and the visual acuity of the left eye was improved to 1.0 (n.c.). No recurrence is observed until now (October 25).

Judgement: Application of Vitronectin eye drops was effective.

2. S. I., 41-year-old male

Disease: Diabetic retinal postoperative erosion of the corneal epithelium

The patient was diagnosed diabetes in 1975. Insulin has been given since 1977. The left vitreum was bleeded in 1987. During 1988 repeated bleeding from the vitreum seriously decreased his visual acuity and he paid the first visit to the hospital attached to Tsukuba University.

Visual acuity, right 1.2 (n.c.), left 0.06 (n.c.)

On Sep. 27, 1988 excision and cerclage of the left vitreum were carried out. Erosion of the corneal epithelium was developed after the operation. The erosion gradually expanded, and on October 17, it expanded over the entire area.

Progress: Application of Vitronectin eye drops (200 µg/ml) started on October 18. In a week after start of the eye drop application epithelium was regenerated over the entire area of the cornea. The regenerated epithelium is slightly pathological at the present (October 26), progress is under observation while continuing the eye drop application. Judgement: Application of Vitronectin eye drops was effective.

EFFECT OF THE INVENTION

As described above, use of vitronectin as an eye drop formulation produces excellent therapeutic effects upon injuries of the corneal epithelium without adverse reaction, efficacy of the Vitronectin as a medicament having been unknown at all.

BRIEF DESCRIPTION OF THE DRAWING

FIG. 1 is a graphical presentation of the cure when the Vitronectin eye drop formulation of the invention was applied.

I claim:

1. An eye drop formulation for treating lesions of the corneal epithelium comprising a Vitronectin solution having a concentration of 0.1 µg/ml–500 µg/ml.

2. An eye drop formulation useful for treating lesions of the corneal epithelium according to claim 1 wherein the Vitronectin is sterilized by autoclaving.

* * * * *

UNITED STATES PATENT AND TRADEMARK OFFICE
CERTIFICATE OF CORRECTION

PATENT NO. : 5,145,680
DATED : September 8, 1992
INVENTOR(S) : Masao Hayashi

It is certified that error appears in the above-identified patent and that said Letters Patent is hereby corrected as shown below:

At column 1, line 7, under the heading Cross-Reference to Related Applications, delete "related to", insert -- a continuation of --.

Signed and Sealed this

Ninth Day of November, 1993

Attest:

BRUCE LEHMAN

Attesting Officer

Commissioner of Patents and Trademarks